(12) United States Patent
Martinez Bellange et al.

(10) Patent No.: US 10,131,961 B2
(45) Date of Patent: Nov. 20, 2018

(54) CAPSULES OF VIABLE BIOMINING MICROORGANISMS, WITH ALGINATE AND IRON IONS CALLED BIOSIGMA BIOLEACHING SEEDS (BBS) AND THEIR USE FOR INOCULATION OF THESE MICROORGANISMS IN BIOLEACHING PROCESSES

(71) Applicant: BIOSIGMA S.A., Colina, Santiago (CL)

(72) Inventors: Patricio Ernesto Martinez Bellange, Santiago (CL); Pilar Angelica Parada Valdecantos, Santiago (CL)

(73) Assignee: BIOSIGMA S.A., Colina, Santiago ( * ) Notice: Subject to any disclaimer, the term of this patent is extended or adjusted under 35 U.S.C. 154(b) by 0 days.

(21) Appl. No.: 14/433,323

(22) PCT Filed: Oct. 9, 2013

(86) PCT No.: PCT/IB2013/059246
§ 371 (c)(1),
(2) Date: Apr. 2, 2015

(87) PCT Pub. No.: WO2014/057443
PCT Pub. Date: Apr. 17, 2014

(65) Prior Publication Data
US 2015/0275324 A1 Oct. 1, 2015

(30) Foreign Application Priority Data
Oct. 11, 2012 (CL) .................................. 2854-2012

(51) Int. Cl.
| | | |
|---|---|---|
| *C12N 1/20* | (2006.01) | |
| *C21B 15/00* | (2006.01) | |
| *C12P 3/00* | (2006.01) | |
| *C12P 39/00* | (2006.01) | |
| *C12N 11/04* | (2006.01) | |
| *C22B 3/18* | (2006.01) | |
| *C12N 11/10* | (2006.01) | |

(52) U.S. Cl.
CPC ................ *C21B 15/00* (2013.01); *C12N 1/20* (2013.01); *C12N 11/04* (2013.01); *C12N 11/10* (2013.01); *C12P 3/00* (2013.01); *C12P 39/00* (2013.01); *C22B 3/18* (2013.01); *Y02P 10/234* (2015.11)

(58) Field of Classification Search
CPC ....................................................... C12N 1/10
See application file for complete search history.

(56) References Cited

U.S. PATENT DOCUMENTS

| | | |
|---|---|---|
| 5,055,402 A | 10/1991 | Greene et al. |
| 5,563,186 A | 10/1996 | Thompson |
| 2008/0044850 A1 | 2/2008 | Taylor et al. |

FOREIGN PATENT DOCUMENTS

| | | |
|---|---|---|
| CN | 1989236 A | 6/2007 |
| WO | 2005/111193 A1 | 11/2005 |

OTHER PUBLICATIONS

Trincone et al., Biotechnology Letters vol. 12 No. 10, pp. 717-720 (1990).*
Bosecker et al., FEMS Microbiology Reviews, vol. 20, Issue 3-4, pp. 591-604, Jul. 1997.*
Brandl, H. (2001) Microbial Leaching of Metals, in Biotechnology: Special Processes, vol. 10, Second Edition (eds H.-J. Rehm and G. Reed), Wiley-VCH Verlag GmbH, Weinheim, Germany).*
Lancy et al., Appl Microbiol Biotechnol (1984) 20: 94-99.*
International Search Report for International Application No. PCT/IB2013/059246 dated May 2, 2014 (1 page).
Rawlings, D., "Heavy Metal Mining Using Microbes", Annu. Rev. Microbiol., 56: 65-91 (2002).
Rawlings, D., "Characteristics and adaptability of iron- and sulfur-oxidizing microorganisms used for the recovery of metals from minerals and their concentrates", Microbial Cell Factories, 4(13): 1-15 (2005).
Sreeram, K.J. et al., "Studies on the nature of interaction of iron(III) with alginates", Biochimica et Biophysica Acta, 1680: 121-125 (2004).
Wu, D. et al., "Lanthanum adsorption using iron oxide loaded calcium alginate beads", Hydrometallurgy, 101: 76-83 (2010).
Yujian, W. et al., "High-rate ferrous iron oxidation by immobilized Acidithiobacillus ferrooxidans with complex of PVA and sodium alginate", Journal of Microbiological Methods, 68: 212-217 (2007).

* cited by examiner

*Primary Examiner* — Irene Marx
(74) *Attorney, Agent, or Firm* — Merchant & Gould P.C.

(57) ABSTRACT

The invention refers to viable biomining microorganisms encapsulated in alginate capsules, called BioSigma Bioleaching Seeds or BBS, wherein the alginate capsules have iron (II) and/or iron (III) ions as the cross-linking cations, and the usage of these capsules in the inoculation of these microorganisms in bioleaching processes.

4 Claims, 9 Drawing Sheets pH 0 pH -0,46 pH -1,16

CAPSULES OF VIABLE BIOMINING MICROORGANISMS, WITH ALGINATE AND IRON IONS CALLED BIOSIGMA BIOLEACHING SEEDS (BBS) AND THEIR USE FOR INOCULATION OF THESE MICROORGANISMS IN BIOLEACHING PROCESSES

This application is a U.S. National Stage Application under 35 U.S.C. § 371 of International Patent Application No. PCT/IB2013/059246 filed 9 Oct. 2013, which claims the benefit of priority to Chilean Patent Application No. 2854-2012 filed 11 Oct. 2012, the disclosures of all of which are hereby incorporated by reference in their entireties. The International Application was published in English on 17 Apr. 2014 as WO 2014/057443.

OBJECTIVE OF THE INVENTION

The invention refers to viable biomining microorganisms encapsulated in alginate capsules, called Biosigma Bioleaching Seeds or BBS, where such alginate capsules have iron ions (II) and/or iron (III) as cross-linking the cations. The invention also refers to the use of these capsules in the inoculation of biomining microorganisms in bioleaching processes.

STATE OF THE ART

Biomining is generally understood as the use of microorganisms for metal recovery from minerals. It is widely known by the term bioleaching, but our understanding of biomining encompasses not only the bioleaching process, but also the monitoring and intervention of the microorganisms involved, since these techniques are complex and are in constant development. We also consider as biominig. the research at laboratory level associated to the improvement of processes or the development of new methodologies.

Bioleaching is defined as a method for the solubilization of metals from complex matrices in an acidic environment using the direct or indirect action of microorganisms. The microorganisms that are useful in these processes, the biomining microorganisms, belong to both Bacteria domain and Archaea domain and fulfill two basic conditions: they are acidophiles and chemolithotrophic. Among the biomining bacteria we can mention the genera *Acidiphilium* sp., *Leptospirillum* spp., *Sulfobacillus* spp. and *Acidithiobacillus* spp., belonging to the latter genus the species *Acidithiobacillus ferrooxidans* and *Acidithiobacillus thiooxidans*. And among the biomining archaeas we can identify the genera *Acidianus* spp., *Ferroplasma* spp., *Metallosphaera* spp., *Sulfolobus* spp. and *Thermoplasma* spp. (Rawlings D E. Annu Rev Microbiol. 2002; 56:65-91; Rawlings D E. Microb Cell Fact 2005; 4(1); 13).

Each one of these microorganisms participates in different chemical reactions which directly or indirectly release to the solution the metal ion of interest. In the direct process the microorganisms act directly over the metal or over its counter-ion, releasing to the solution, in both cases, an ion of the metal of interest. On the other hand, in the indirect process the microorganism generates the chemical conditions that favour metal solubilization, either by the acidification of the medium, by forming sulphuric acid, or by the generation of an oxidizing agent, such as iron (III). For example, the sulfoxidizing biomining microorganisms such as *Acidithiobacillus thiooxidans* oxidize sulphur generating sulphuric acid.

In the bioleaching mechanisms iron plays a very important role. Iron (III) is a powerful oxidizing agent, which in acid medium oxidizes the insoluble metal sulfides generating biosulphate, sulphate and elemental sulphur (S°) as main products. The reaction also releases the metal as a cation to the solution, and iron (III) is then reduced to iron (II). The iron (II) generated in this reaction can be reoxidized by iron-oxidizing biomining microorganisms such as *Acidithiobacillus ferrooxidans, Leptospirillum* spp., *Sulfobacillus* spp. and *Ferroplasma* spp., regenerating the iron (III). (Rawlings D E Annu Rev Microbiol 2002; 56:65-91, Rawlings D E Microb Cell Fact 2005; 4(1), 13).

The tradicional mining practice of the bioleaching processes is to keep the mineral in acidic conditions and subsequently to stockpile and to irrigate the ore with solutions that contain sulphuric acid, reaching pH measurements that are extremely acid. Those are the environmental conditions where the inoculation of the mineral is made with the biomining microorganisms. Often the mineral pH at the time of the inoculation is still too acid for the survival of the microorganisms, and many of them die because of the adverse environmental conditions. From this process arises the the need for protecting the inoculated microorganisms from those extreme environmental conditions, such as the highly acidic environment that is present at certain stages of the process, or the toxic chemicals that could be present in the same mineral or in solutions that are added to the mineral further during bioleaching, for example the raffinate.

The inventors have solved this technical problem by providing viable biomining microorganisms encapsulated in alginate capsules, called BioSigma Bioleaching Seeds or BBS. Such alginate capsules contain biomining microorganisms and iron cations Fe (II) and/or Fe(III). The pH of these capsules is between 1 and 2 in accordance with the acidophilic conditions needed for the biomining microorganisms. It has been found that the capsules of the invention allow the inoculation of the mineral to be bioleached with viable microorganisms, facilitating their handling and preserving their integrity during transportation and homogeneous inoculation. It also, protects and facilitates the adaptation of the microorganisms to toxic chemicals present in the process, as well as to the extremely acidic environment present in the initial stages of the process. Surprisingly it also has been found that Fe(II), in spite of being in the intercrossed structure of the alginate, is bioavailable and acts as substrate for the iron oxidizing biomining microorganisms. On the other hand, it has been demonstrated that additives can be incorporated in these capsules for the microorganisms, such as, for example, substrates that are used as energy sources, such as organic compounds and particulate or soluble sulphur (i.e. tetrathionate or thiosulphate). The additives added would be used to favor the microorganism growth of the same BBS inoculum, for instance if sulfur oxidizing microorganisms are inoculated, tetrathionate or thiosulphate can be incorporated to the BBS as energy sources for such microorganisms, which can also allow a greater production of sulphuric acid.

Alginate is formed by D-mannuronic and L-guluronic acids and is obtained from a marine brown algae (Phaeophyceae). At environmental temperatures and in the presence of divalent cations such as $Ca^{2+}$, $Ba^{2+}$, alginate becomes a gel by an irreversible reaction. Alginate has traditionally been used to encapsulate viable microorganisms. The usual practice in microorganisms encapsulation with alginate is to obtain a suspension of the microorganisms to be encapsulate in sodium alginate, them to add this suspension, drop by drop and with slight agitation, to another solution with divalent cations, such as $Ca^{2+}$ ion, where alginate pearls are formed with the encapsulated microorganisms. The microorganisms encapsulated this way have been used in agriculture, industrial and laboratory processes.

Very little literature background exists in the state of the art related with the matter of the invention. For example, we found the publication of K. J. Sreeram (K. J. Sreeram et al Biochimica at Biphysica Acta 1670 (2004) 121-125) that studies the interaction between alginate and Fe (III), where it is indicated that at pH 3.5 a colloidal union is formed, which does not precipitate and it is stable. In this publication the interaction between alginate and Fe (III) is not used to encapsulate microorganisms, no alginate precipitates are observed and the range of working pH is different. As a conclusion, the publication mentioned above does not affect the subject of this invention.

On the other hand we found the publication of E. D. Lancy and O. Y. Tuovinen, (E. D. Lancy and O. Y. Tuovinen, Appl. Microbial. Biotechnol. (1884) 20:94-99) where *Acidithiobacillus ferrooxidans* is immobilized in a matrix of calcium alginate and is used for the oxidization of Fe (II) to Fe (III). This publication does not suggest the encapsulation using Fe (II) or Fe (III) as the cross-linking agent for alginate. Also the publication of Lancy and Touvinen aims to immobilize the microorganisms to study the rate of iron oxidization, while the present invention aims to encapsulate the microorganisms to use them as inoculum in bioleaching processes. This dissimilarity is important, and as it will be better discussed later, for the object of this invention it is relevant that the encapsulated microorganisms are able to leave the capsules to colonize the mineral that will be bioleached. For this reason, the proportion of alginate used to encapsulate the microorganisms in the invention it is lower than the proportion of alginate used to immobilize the microorganisms in the publication mentioned above. An additional differentiation is the fact that this invention encapsulates biomining microorganisms, within those there is *Acidithiobacillus ferrooxidans*, however it is not the only type of microorganism to be encapsulated. In synthesis the publication of Lancy and Touvinen does not anticipate this present invention.

DESCRIPTION OF THE INVENTION

Figure 1:
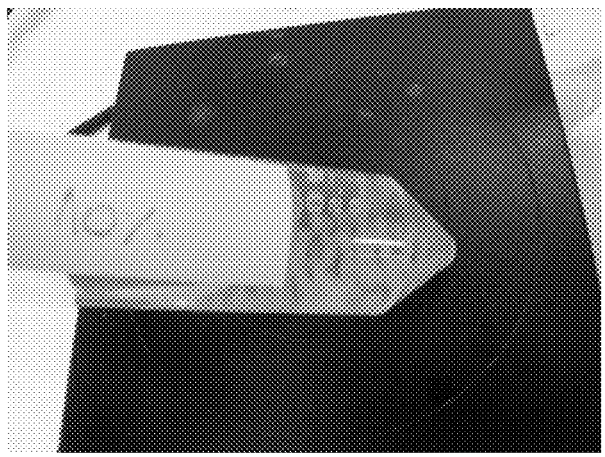
FIG. 1—Acid resistance of BBS at different concentrations of sulfuric acid. BBS maintain their integrity at concentrations of up to 25% of sulfuric acid, which corresponds to of pH of −0.46. On the other hand, at concentrations of 50% of sulfuric acid, at pH of −1.16, the BBS are disintegrated.
Figure 1:
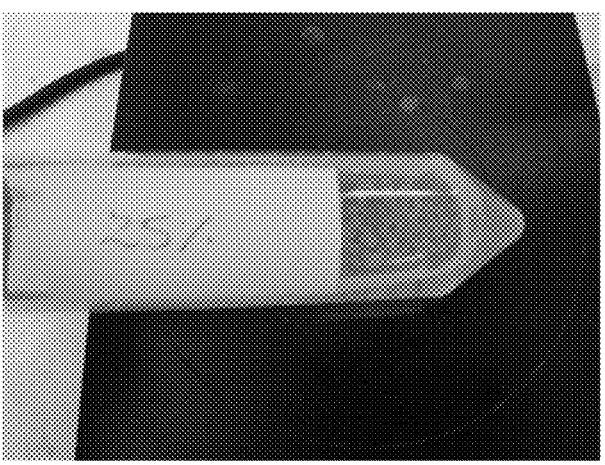
Figure 1:
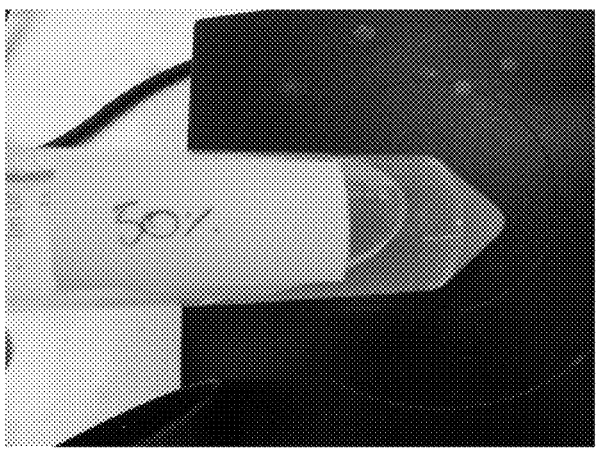

The present invention describes viable biomining microorganisms encapsulated in alginate capsules, called Bio-Sigma Bioleaching Seeds or BBS, where such capsules comprise a matrix of alginate and iron cations, either Fe(II) or Fe(III), which contain the biomining microorganisms. The pH of these capsules is between 1 and 2, according to the acidophilic conditions necessary for the biomining microorganisms. It has been found that the Fe(II), in spite of being in the cross-linking agent of alginate, is bioavailable and acts as substrate for encapsulated biomining iron oxidizing microorganisms. One advantage of these capsules is that they allow the microorganism inoculation to the mineral to be bioleached. The capsules facilitate the microorganisms handling and they preserve their integrity during transportation and inoculation, protecting the microorganisms from toxics present in the process, as well as extremely acid environments. Another advantage of the BBS is related to the storage of the microorganisms, since we have found that the microorganisms remain viable for years, in the same proportions they were encapsulated and without contamination. All the above represents a clear operational advantage on the existing methods of microorganisms inoculation, where the solutions that comprise the inoculum must be transported and incorporated.

Within the bioleaching processes, a key step is the inoculation of the mineral to be bioleached with biomining microorganisms. Notwithstanding its importance, there are several problems associated to this step, for example, how to achieve the homogeneous inoculation in the entire mineral to be bioleached. Moreover, the toxins present in the process, either in the mineral or in the acidifying solutions (as raffinate or highly acid solutions), can affect the cellular viability, the generation of microorganisms consortia, which are made according to the mineral to be bioleached, and the handling of the microorganisms to be inoculated in the biomining operation.

The traditional inoculation process of a bioleaching heap consists in irrigating the heap with sulfuric acid or other acid solution available in the operation and subsequently irrigate the heap with an inoculation solution which contains the biomining microorganisms. In this process the microorganisms are directly exposed to the extremely acid medium, with pH values under 1, and to the toxic chemicals which are either in the mineral to be bioleached or in the solutions used to irrigate the mineral, for example raffinate, which affects cellular viability and decimates the inoculated bacteria.

Likewise, this method of inoculating microorganisms through irrigation has the disadvantage that it does not ensure homogeneous inoculation of the entire mineral. The permeability in the heap is not homogeneous because the minerals that form it have an irregular conformation. This makes the natural flow of the inoculation solution produce pseudo-channels in the inner part of the heap, creating sectors where the inoculation is successful and others within the same heap, where the inoculating solution cannot not reach.

It is common that the microorganisms that are the most adequate to bioleach a mineral in particular, are actually a consortium of different specific microorganisms. These consortia can be grown in laboratory, but the desired ratio of each microorganisms in the inoculation solution is not always as expected, as the growth of some microorganism species often prevails over others.

Finally the conventional inoculation has problems in the handling of the inoculation solution, which is liquid, and it must be generated in reactors within the same operation and transported by pipes or hoses to be able to inoculate the mineral.

All the problems mentioned above are solved by this invention since the inventors have demonstrated that the invention capsules, BioSigma Bioleaching Seeds or BBS, protect the microorganisms from both the extreme acidity and the toxins.

Moreover, as BBS are solid particles, they can be mixed with the mineral before stockpiling the heap, ensuring a homogeneous inoculation in the entire mineral, which increases the efficiency of the inoculation process and therefore the efficiency of bioleaching.

The capsules of the invention, BioSigma Bioleaching Seeds may contain any microorganism or groups of microorganisms encapsulated at different ratios, as desired. They allow obtaining the consortia of specific encapsulated microorganisms to be able to homogeneously inoculate minerals that also have specific characteristics.

Finally, as they are solid capsules they do not necessarily need to be generated in the same working area where the bioleaching is being done, and the problems associated to the transportation of the microorganisms to be inoculated are reduced.

Additionally, the BBS can also contain, apart from the microorganism nutrients, additives or preservatives that permit an enhanced microbial activity.

The BBS allow the encapsulation of any kind of biomining microorganism, either as a single cell cultures or in microorganism consortia, as the microorganism consortium being understood as both a consortium that is stable over time and also the simple operational combination of two or more single cell cultures obtained traditionally. Within the biomining microorganisms are: *Acidiphilium* spp., *Leptospirillum* spp., *Sulfobacillus* spp., *Acidithiobacillus* spp, specifically *Acidithiobacillus ferrooxidans* and *Acidithiobacillus thiooxidans*; *Acidianus* spp., *Ferroplasma* spp., *Metallosphaera* spp., *Sulfolobus* spp. and *Thermoplasma* spp.

The BBS allow obtaining concentrations of encapsulated biomining microorganisms of over $10^3$ microorganisms/g of capsules, specially over $10^5$ microorganisms/g of capsules, and preferentially over $10^7$ microorganisms/g of capsules.

The method to generate BioSigma Bioleaching Seeds or BBS starts with obtaining a culture of biomining microorganisms, either a single cell culture or a consortium, in concentrations of over $10^3$ microorganisms/mL, especially over $10^5$ microorganisms/mL and preferentially over $10^7$ microorganisms/mL. The cultured cells are added by filtration or centrifugation to the solution of alginate in the desired concentration that can be over $10^3$ microorganisms/mL of solution to be encapsulated, especially over $10^5$ microorganisms/mL of solution to be encapsulated and preferentially over $10^7$ microorganisms/mL of solution to be encapsulated. The alginate concentration is between 0.2% and 3%, preferentially at 1.5% to form a solution of microorganisms and alginate, with a final alginate concentration between 0.2% and 3%, preferentially at 1%. The ratio between the alginate solution and the solution of biomining microorganisms to be encapsulated can vary between 4:1 and 1:4 in volume. Optionally nutrients, additives and preservatives can be added, such as metabolites, proteins, organic molecules and/or inorganic molecules and elements, etc.

This mixture of microorganisms, alginate and optionally nutrients, additives or preservatives forms the solution that will be encapsulated. The solution to be encapsulated is added drop by drop and under smooth agitation to a solution of Fe(II) and/or Fe(III), which constitutes the spherification agent. The capsules are formed by contact of the solution to be encapsulated with the spherification agent, obtaining the BioSigma Bioleaching Seeds (BBS).

The spherification solution comprises either Fe(II) and/or Fe(III) sulfate in concentrations from 0.1 g/L to 30 g/L. The combination where ferric sulphate represents 60 to 90% and ferrous sulphate represents between 40 and 10% relative in the solution is preferred.

When the capsules comprise Fe (II) as the cross-linking cation, either alone or in combination with Fe (III), the Fe (II) can also act as substrate for the iron oxidizing microorganisms, such as *Acidithiobacillus ferrooxidans, Leptospirillum* spp., *Sulfobacillus* spp. and *Ferroplasma* spp. encapsulated in the BBS.

The inventors have discovered that when encapsulating a complex consortium of microorganisms the ratio of the microorganism species within the BBS is similar to the ratio in the inoculum (see example 1) and therefore it is considered that the encapsulation is not selective for any type of microorganism in particular.

As the inoculation of biomining microorganisms in the bioleaching process occurs in extremely acidic environments, the resistance of BBS was proven by exposing them directly to sulphuric acid. The results are shown in FIG. 1. It is observed that the BBS maintain their integrity when up to 25% of sulphuric acid is added, which corresponds to a pH of −0.46. On the other hand, the BBS are disintegrated when exposed to concentrations of 50% of sulphuric acid at a pH of −1.16. As the microorganisms without any protection can resist a pH near 1, the BBS can grant an additional protection for a pH of up to −0.46.

Figure 2:
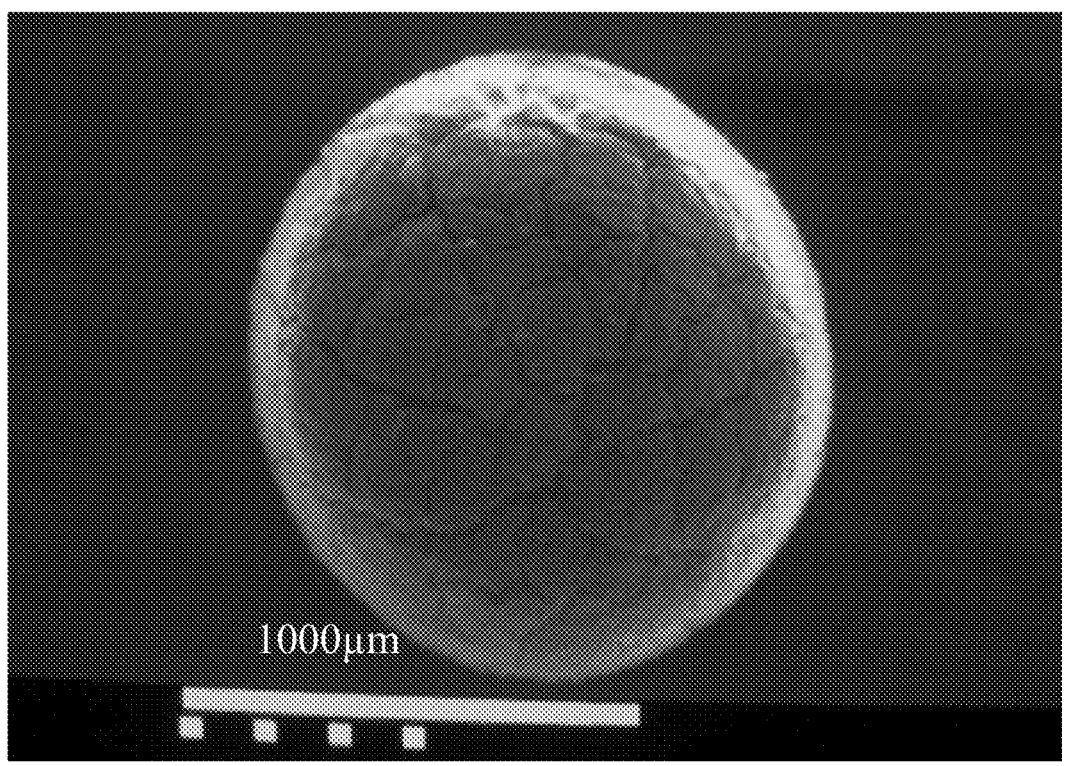
FIG. 2. Scanning electron microscopy of a complete BBS with a magnification of 45× (the lower bar corresponds to 1 mm).

The BioSigma Bioleaching Seeds (BBS) were studied by scanning electron, transmission and light microscopy techniques, and it was determined that the matrix of alginate and iron permit the proliferation, the traffic and adherence of the microorganisms. FIG. 2 shows an entire BBS with the microorganism Wenelen DSM 16786, an *Acidithiobacillus*

Figure 3:
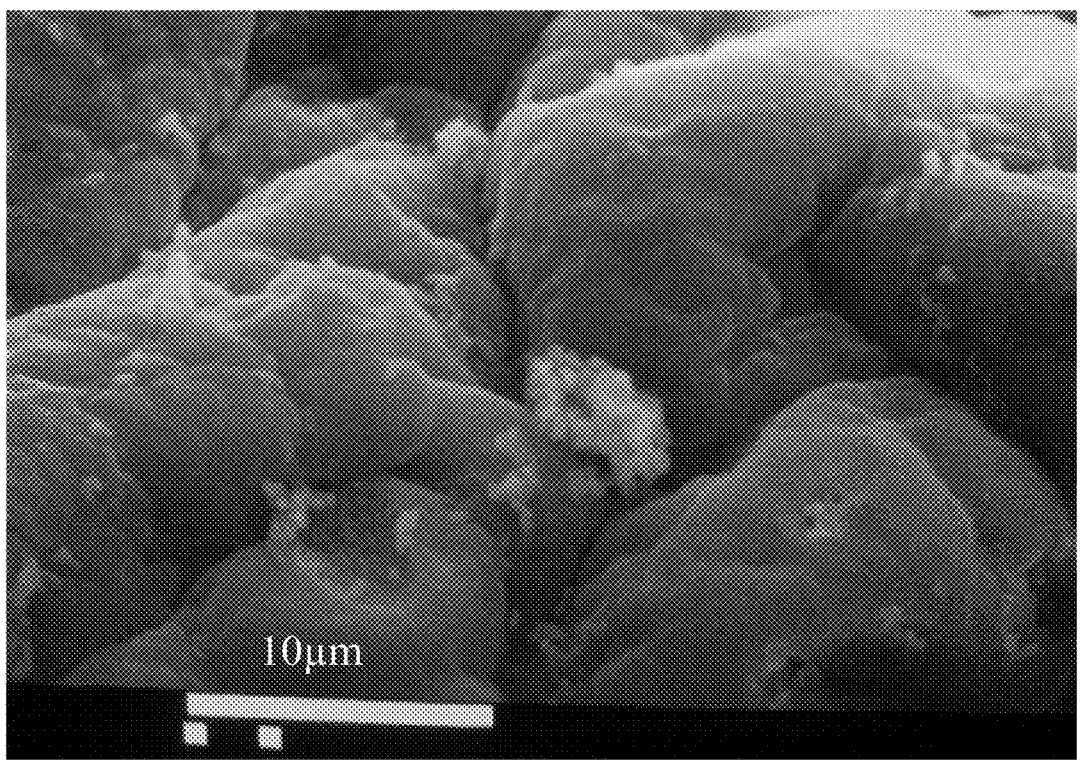
FIG. 3. Scanning electron microscopy of the surface of a BBS with a magnification of 3000× (the lower bar corresponds to 10 μm). Microorganisms colonizing the surface of the BBS can be observed.
Figure 4:
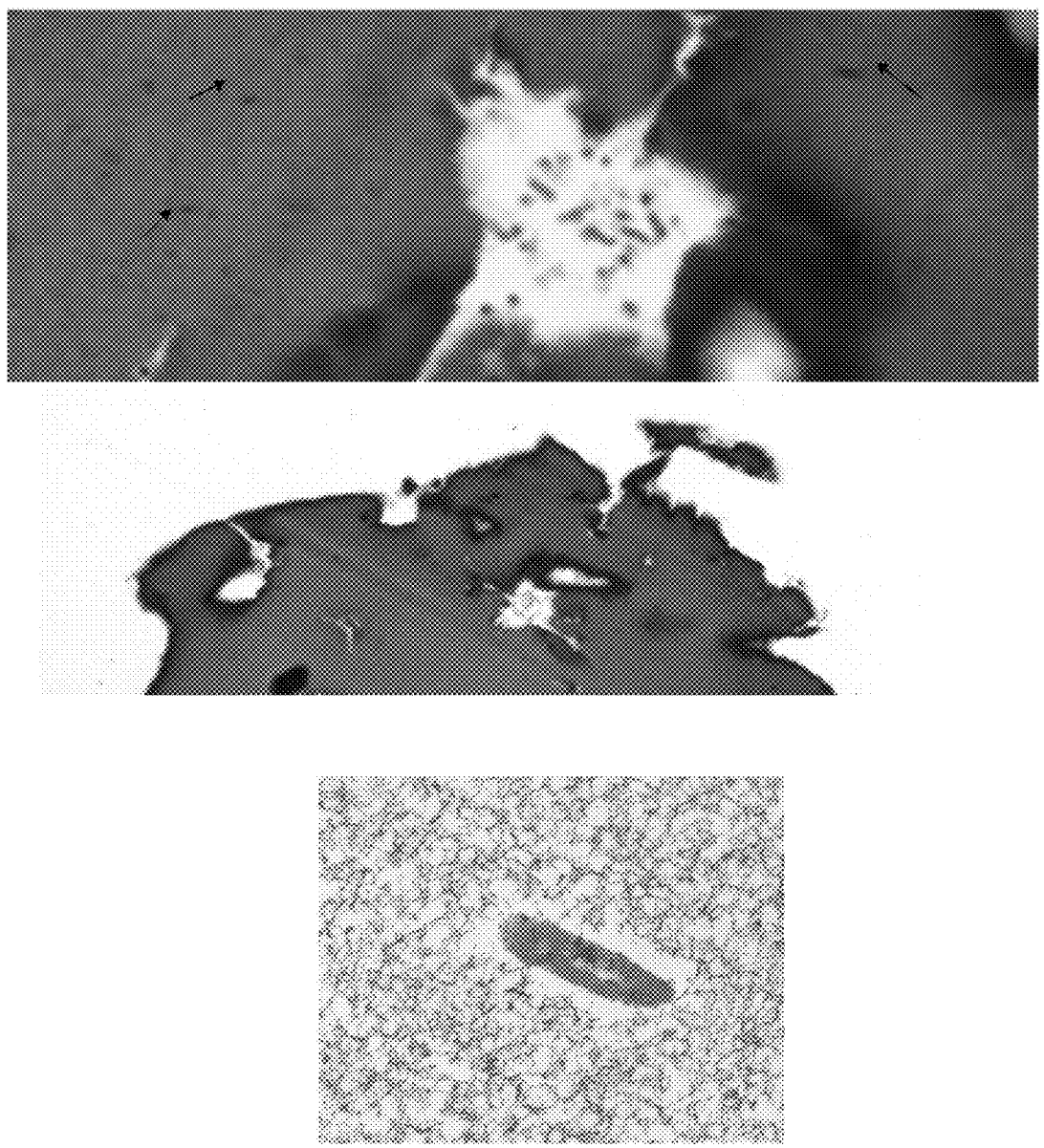
FIG. 4. Light microscopy of a transversal cut of a stained BBS, with a magnification of 400×. The microorganisms are encapsulated within the BBS and can colonize lumens that are part of their structure.

*ferrooxidans* strain, property of BioSigma SA, where it is observed that the BBS presents ridges on its structure. FIG. 3 shows that there is colonization of the microorganisms over the surface of the BBS, which implies that the surface of the BBS allow adherence of the biomining microorganisms. Likewise, FIG. 4 shows a transversal cut of a BBS where the encapsulation of microorganisms within the BBS can be observed. The encapsulated microorganisms would be presented on both: the matrix of alginate and in interstices with microclimates isolated from the outdoor environmental conditions.

When using the BBS to inoculate mineral, these can be used in a ratio between 0.01%-99% in weight per gram of mineral, preferentially in a ratio between 0.01 to 50% and in especial conditions in a ratio of between 0.01 to 10%.

The BBS can be used to inoculate any media or system that requires the presence of biomining microorganisms, such as a bioleaching heap, a bioleaching reactor, a reactor of biomass generation, a flask, a bioleaching column, or other. An important additional advantage is that the BBS can be stored for a long time (years), without deteriorating the microorganisms inside it and without losing their activity or being contaminated by other species apart from the BBS.

The medium or system inoculated with BBS operates in the usual way that is to say in the same way in which an inoculated system would operate in the traditional way with liquid cultures of biomining microorganisms.

EXAMPLES

Example 1. Encapsulation of a Consortium of Microorganisms

A consortium of microorganisms constituted by *Acidithiobacillus thiooxidans*, *Leptospirillum* spp., *Acidiphilium* spp., *Ferroplasma* spp. and Wenelen DSM 16786 (strain of *Acidithiobacillus ferrooxidans* property of BioSigma SA.) was obtained. The concentrations of these microorganisms in the inoculum used were determined by qPCR as shown on Table 1.

The cells were recollected by filtration and were washed twice in media KMD (($NH_4$)$_2$$SO_4$, 247.5 mg/L; $NaH_2PO_4 \cdot H_2O$, 36.5 mg/L; $KH_2PO_4$, 13.125 mg/L; $MgSO_4 \cdot 7H_2O$, 25 mg/L; $CaCl_2$, 5.25 mg/L) and were finally resuspend in 4 ml of KMD medium. The 4 ml containing the consortium were mixed with 6 mL of sodium alginate at 1.5% to form the solution to be encapsulated. The resulting solution was added drop by drop from a burette to a solution of 9 g/L of total iron with a proportion of 60% of ferric ions (Fe(III)) and 40% of ferrous ions (Fe(II)), applying slight agitation in a magnetic agitator and thus forming the BBS.

To determine the concentration of microorganisms in the BBS an aliquot was taken from the BBS formed, which was dissolved in a solution of ethanol 70%. DNA was extracted and the concentration of each one of the microorganisms present was determined by qPCR. The results are shown on Table 1.

TABLE 1

| Microorganism | Inoculum (microorganisms/mL) | BBS (microorganisms/mL) |
| --- | --- | --- |
| Total Bacteria | $3.54 \times 10^8$ | $7.77 \times 10^7$ |
| *A. ferrooxidans* | $1.00 \times 10^3>$ | $1.00 \times 10^3>$ |
| *A. thiooxidans* | $5.99 \times 10^7$ | $9.74 \times 10^6$ |
| *Leptospirillum* spp. | $7.93 \times 10^5$ | $1.00 \times 10^3>$ |

TABLE 1-continued

| Microorganism | Inoculum (microorganisms/mL) | BBS (microorganisms/mL) |
| --- | --- | --- |
| *Acidiphilium* spp. | $4.91 \times 10^4$ | $1.00 \times 10^3>$ |
| *Ferroplasma* spp. | $2.15 \times 10^7$ | $3.42 \times 10^6$ |
| Wenelen DSM 16786 | $1.00 \times 10^3>$ | $1.00 \times 10^3>$ |

The results show that the encapsulation is not selective for any specific type of microorganisms as the proportion of each specie is similar to that of the inoculum to be encapsulated. The results indicate that the BBS formed from a microbiological consortium are representative of such consortium. The minor differences are explained by the lower efficiency in DNA extraction from the BBS.

Example 2. Cell Activity in the BBS

Figure 5:
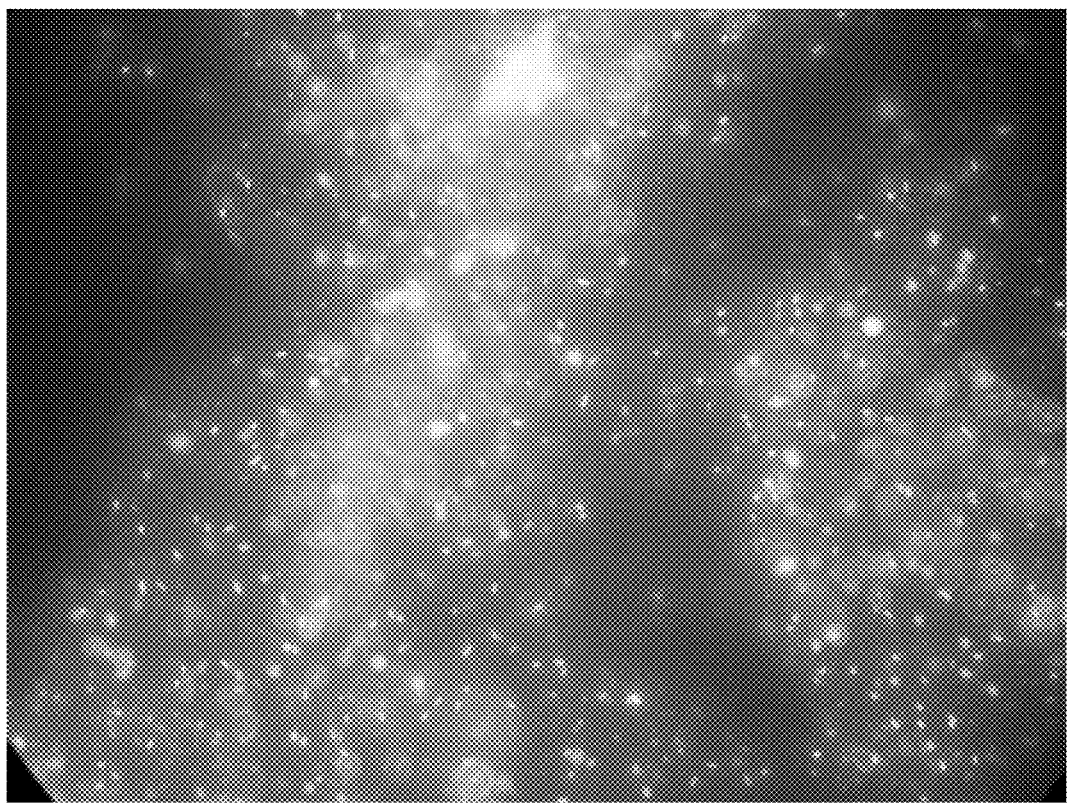
FIG. 5. Fluorescence microscopy of a transversal cut of a BBS stained with LIVE/DEAD® BacLight™ kit from Life technologies. The stain dyes live cells in green and dead cells in red. In this figure no red dyed cells were found, and all the marks correspond to live cells.

Some of the BBS formed in example 1 were stained with the LIVE/DEAD® BacLight™ kit from Life Technologies, according to the instructions of the manufacturer. This kit dyes the live cells green and the dead cells red. In this case, no red cells were found. FIG. 5 shows the active cells inside the BBS, leading to the conclusion that the encapsulated microorganisms in the BBS continue to be active.

Example 3. Cell Viability

To determine if the BBS are useful in the inoculation of microorganisms, the concentration of microorganisms was compared in the culture media of 1% S° KMD (($NH_4$)$_2$$SO_4$, 247.5 mg/L; $NaH_2PO_4 \cdot H_2O$, 36.5 mg/L; $KH_2PO_4$, 13.125 mg/L; $MgSO_4 \cdot 7H_2O$, 25 mg/L; $CaCl_2$, 5.25 mg/L) inoculated directly with *Acidithiobacillus thiooxidans* or in the BBS encapsulated with *Acidithiobacillus thiooxidans*.

Figure 6:
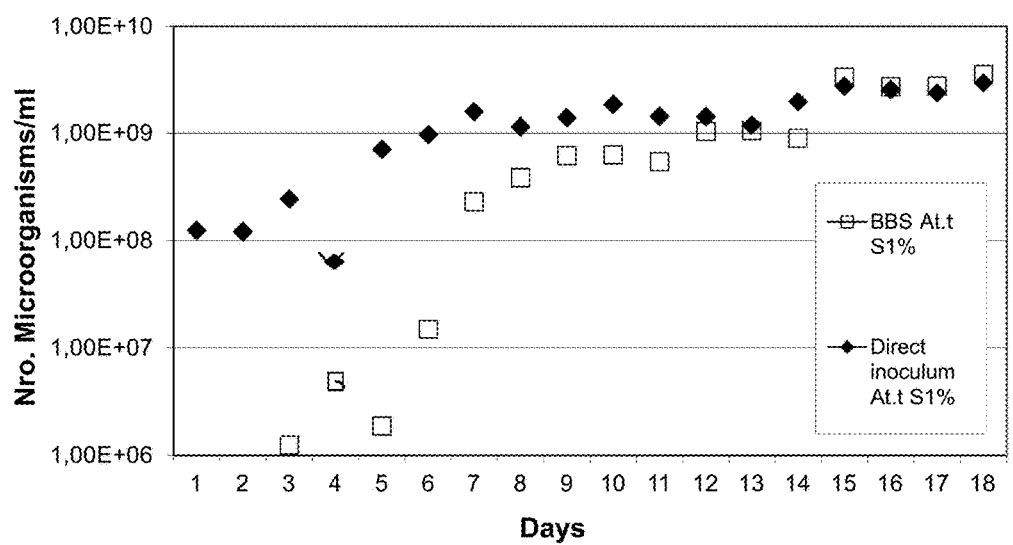
FIG. 6. Chart representing in black diamonds the concentration of *Acidithiobacillus thiooxidans* (At.t) in the supernatants of cultures inoculated with $1.0 \times 10^8$ microorganisms/mL of an inoculum of *A. thiooxidans* versus the open squares representing an equivalent concentration of encapsulated *A. thiooxidans* in BBS, and their growth behavior on time.

In a flask containing 500 mL of 1% S° KMD culture medium $1 \times 10^8$ microorganisms/ml of *Acidithiobacillus thiooxidans* were inoculated. In a second flask containing 500 mL of 1% S° KMD culture medium 5 mL of BBS with *Acidithiobacillus thiooxidans* encapsulated were inoculated at a concentration equivalent to the first flask. The microorganism concentration in the supernatant was measured daily during 18 days, the results are shown on FIG. 6.

As expected, no microorganism was observed in the culture in the first days of inoculation with BBS. Notwithstanding in the $3^{rd}$ day after inoculation concentrations higher than $10^6$ microorganisms/ml were observed for *Acidithiobacillus thiooxidans*. From day 12 on the concentration of microorganisms in the supernatant of both cultures were evened.

This shows that the BBS allow the cellular viability of the encapsulated microorganisms. Also the it shows that the microorganisms are capable of leaving the BBS to colonize the surrounding medium. That is to say, it shows that the BBS are useful as inoculation agents.

Example 4. Inoculation of Bioleaching Columns

To determine if the BBS are effective in the inoculation of microorganisms during bioleaching processes, 4 columns of mineral were prepared to be bioleached at laboratory scale. The columns were submitted to different inoculation conditions, firstly with the conventional inoculation method by irrigation of microorganisms culture and secondly with inoculation with the BBS formed in example 1. The conditions of each column are described below:

4 columns of 30 cm of high and 5.75 cm of diameter, were prepared with 500 g of crushed mineral with a granulometry of ½" (1.27 cm). Once the columns were inoculated, the effluent solution was recirculated to the column (closed circuit).

Column 1. Inoculation by Irrigation (Conventional)

The mineral was agglomerated with acid water at pH1.4 which is equivalent to 5% humidity. An inoculum solution was prepared with 1 mL of the same consortium used to form the BBS of example 1, at a concentration of $1 \times 10^6$ microorganisms/ml and it was diluted in 99 mL of a solution of 3 g/L Fe(II) and medium KMD (($NH_4$)$_2SO_4$, 247.5 mg/L; $NaH_2PO_4.H_2O$, 36.5 mg/L; $KH_2PO_4$, 13.125 mg/L; $MgSO_4.7H_2O$, 25 mg/L; $CaCl_2$, 5.25 mg/L), at pH 1.4.

The 100 ml solution previously prepared was used to inoculate the column in an open circuit. After the inoculation step, the circuit was closed. In the column, the recirculation solution was the accumulated effluent from the inoculation stage plus the required volume to reach 1000 mL of a solution of 3 g/L Fe(II) and medium KMD (($NH_4$)$_2SO_4$, 247.5 mg/L; $NaH_2PO_4.H_2O$, 36.5 mg/L; $KH_2PO_4$, 13.125 mg/L; $MgSO_4.7H_2O$, 25 mg/L; $CaCl_2$, 5.25 mg/L), pH 1.4.

Columns 2, 3 and 4: Inoculation by BBS.

The mineral was agglomerated with acid water at pH 1.4, which is equivalent to 5% humidity. Firstly 50% of the acid water solution of was added (equivalent to 2.5% humidity) and it was mixed homogeneously by rolling the mineral over a plastic surface. Different volumes of BBS prepared in the same way as described on example 1 were added to each column: 5 mL in column 2 (BBS at 1%), 10 mL in column 3 (BBS at 2%) and 20 mL in column 4 (BBS at 4%) and mixed homogeneously. The concentration of microorganisms added to the mineral corresponds to $1 \times 10^6$ microorganisms/g of mineral. The other 50% of the acid water solution was then added and mixed homogenously.

The circuit was closed with 1000 mL of a solution of Fe(II) 3 g/L and medium KMD (($NH_4$)$_2SO_4$, 247.5 mg/L; $NaH_2PO_4.H_2O$, 36.5 mg/L; $KH_2PO_4$, 13.125 mg/L; $MgSO_4.7H_2O$, 25 mg/L; $CaCl_2$, 5.25 mg/L), pH 1.4.

Figure 7:
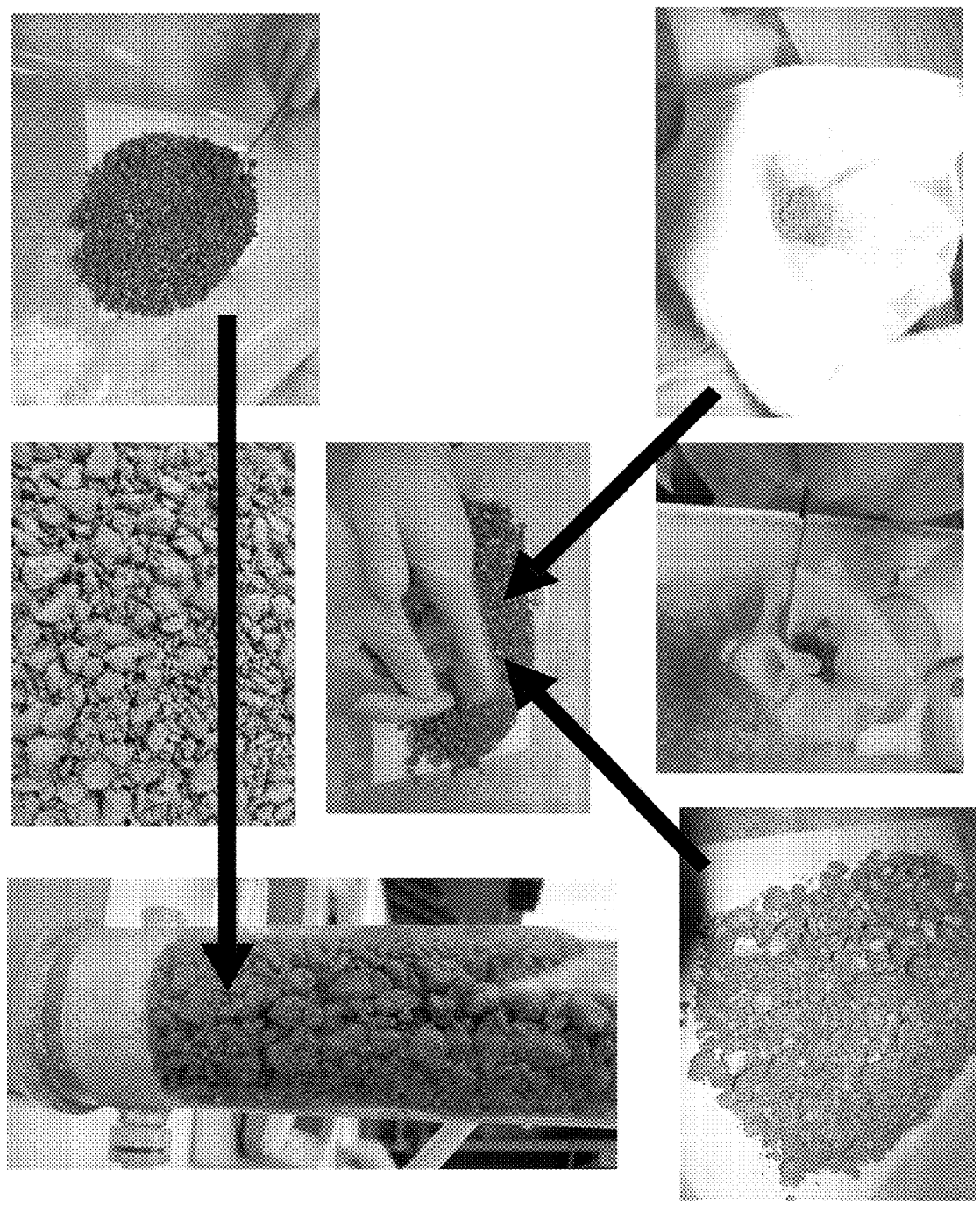
FIG. 7. Incorporation of BBS in a column of mineral to be bioleached.

FIG. 7 shows the BBS in the column.

Figure 8:
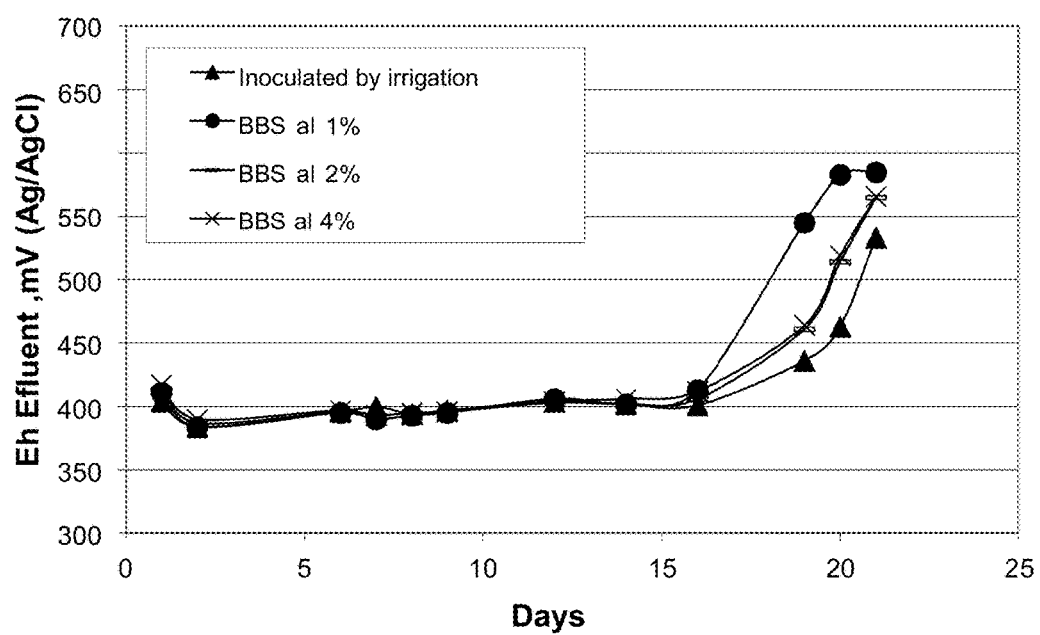
FIG. 8. Comparison of the bioleaching activity in different inoculation conditions measured electrochemically by the redox potential (Eh, mV Ag/AgCl). Column 1 inoculated by irrigation with $1.0 \times 10^6$ microorganisms/g of mineral, column 2 inoculated $1.0 \times 10^6$ microorganisms/g of mineral in 5 ml of BBS (1%), Column 3 inoculated with $1.0 \times 10^6$ microorganisms/g of mineral in 10 ml of BBS (2%), Column 4 inoculated with $1.0 \times 10^6$ microorganisms/g of mineral in 20 ml of BBS (4%). Bioleaching activity is higher in the columns inoculated with BBS than in the column inoculated by irrigation. The inoculation with 1% of BBS in mineral shows the best performance.

After the irrigation of the four columns has started, those remained in recirculation mode and the redox potential of the solution was measured daily (Eh, mV, Ag/AgCl), giving an indication of the bioleaching activity (oxidation of ferrous ion). The results are shown on FIG. 8. It is observed that the redox potential of the effluent solutions of the columns inoculated with BBS (in all different concentrations) increases faster (shorter operation time) than the column inoculated conventionally. This corresponds to a greater activity of the microorganisms inside the column, demonstrating the advantage of using this inoculation method.

Example 5. Inoculation of Bioleaching Columns in Presence of Toxins

To determine whether the BBS are effective for the inoculation of microorganisms in bioleaching processes under toxic conditions, two mineral columns were prepared for bioleaching at laboratory scale. The columns were submitted to different inoculation conditions; firstly with the conventional inoculation by irrigation with the culture and secondly with inoculation with the BBS prepared as in example 1, using a method very similar to that described in example 4. 1% in weight of BBS per gram of mineral was added to the column inoculated with BBS. To evaluate the effect of the toxins on the BBS, 500 mL of the recirculating solution composed by Fe (II), 3 g/L and medium KMD (($NH_4$)$_2SO_4$, 247.5 mg/L; $NaH_2PO_4.H_2O$, 36.5 mg/L; $KH_2PO_4$, 13.125 mg/L; $MgSO_4.7H_2O$, 25 mg/L; $CaCl_2$, 5.25 mg/L) at pH 1.4, was replaced by raffinate that is formed mostly by Cu, Fe (III), Fe(II), $SO_4$-2, Cl— and heavy metals.

Figure 9:
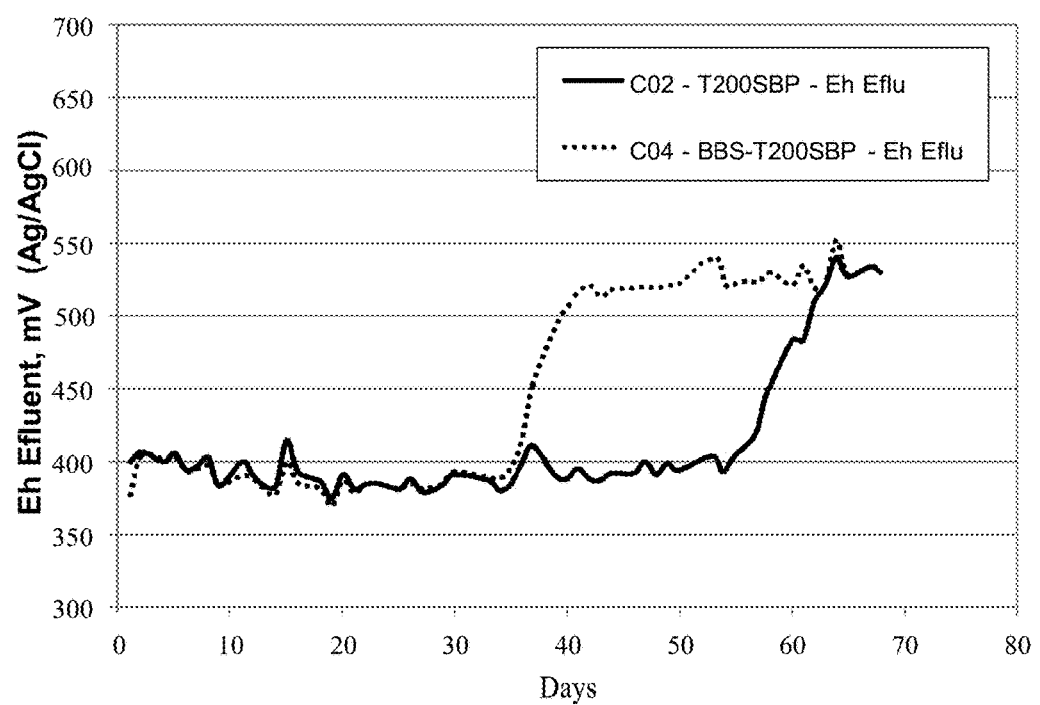
FIG. 9. Comparison of bioleaching activity in different inoculation conditions in the presence of raffinate: column C02, inoculated by irrigation with $1.0 \times 10^6$ micro organisms/g of mineral, column C04 inoculated with $1.0 \times 10^6$ microorganisms/g of mineral in 1% of BBS. Bioleaching activity starts 20 days earlier in the column inoculated with BBS when compared with to that the one inoculated by irrigation.

Once the two columns were set they were maintained in recirculation mode and Eh values were measured daily. The results are shown in FIG. 9. It is observed that the column inoculated with BBS starts its bioleaching activity around 20 days earlier than the column inoculated conventionally. This shows that the BBS acts protecting the microorganisms from the toxins present in the medium, permitting in this way their adaptation and subsequent colonization of the mineral with the corresponding bioleaching activity.

We claim:

1. A method of increasing bioleaching rate in a heap or dump under toxic conditions for microorganisms, wherein the method comprises the following steps:
   a) providing "BioSigma Bioleaching Seeds" (BBS) capsules that comprise a consortium of viable microorganisms in a matrix of alginate and iron ions, whether Fe(II) or Fe (III) or a mixture thereof and used as cross-linking cations, wherein the BBS capsules comprise a mixture of a solution of sodium alginate at a concentration of 0.2% to 3% with a suspension of microorganisms in a ratio of 4:1 to 1:4 by volume, and being the BBS capsules in a spherification solution that comprises Fe(II) or Fe(III) ions, or a mixture thereof; and
      wherein the consortium of microorganisms is present inside the BBS capsules in concentrations above $10^3$ microorganisms/mL of the solution of sodium alginate; and
      wherein the consortium of microorganisms is constituted by at least $1.00 \times 10^3$ microorganisms/mL of *Acidithiobacillus ferrooxidans* Wenelen DSM 16786, at least $9.74 \times 10^6$ microorganisms/mL of *Acidithiobacillus thiooxidans*, at least $1.00 \times 10^3$ microorganisms/mL of *Acidiphilium* spp., at least $1.00 \times 10^3$ microorganisms/mL of *Leptospirillum* spp., and at least $3.42 \times 10^6$ microorganisms/mL of *Ferroplasma* spp.;
   b) inoculating an ore in a bioleaching heap or dump with a proportion of BBS capsules between 0.01% and 99% by dry weight per gram of ore to form a homogeneous mixture of inoculum and ore, and then stockpiling the heap or dump after the inoculation is performed; and
   c) irrigating the stockpiled heap or dump with an irrigation solution comprising water and raffinate, wherein the raffinate is formed by Cu, Fe (III), Fe(II), $SO_4$-2, Cl— and heavy metals.

2. The method of claim 1, wherein the spherification solution comprises a total iron concentration of 0.1-30 g/L and a composition of 10-40% Fe (II) and 60-90% Fe(III).

3. The method of claim 1, wherein nutrients, additives or preservatives are added to the spherification solution prior to the generation of BBS capsules.

4. The method of claim 2, wherein nutrients, additives or preservatives are added to the spherification solution prior to the generation of BBS capsules.

* * * * *